(12) United States Patent
Feldman et al.

(10) Patent No.: US 8,080,153 B2
(45) Date of Patent: Dec. 20, 2011

(54) ANALYTE DETERMINATION METHODS AND DEVICES

(75) Inventors: Benjamin J. Feldman, Oakland, CA (US); Yi Wang, San Ramon, CA (US); Ting Chen, Austin, TX (US); Lam Tran, Valejo, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 868 days.

(21) Appl. No.: 12/129,423

(22) Filed: May 29, 2008

(65) Prior Publication Data

US 2009/0000959 A1 Jan. 1, 2009

Related U.S. Application Data

(60) Provisional application No. 60/941,152, filed on May 31, 2007.

(51) Int. Cl.
*C12M 1/00* (2006.01)
*C12Q 1/00* (2006.01)

(52) U.S. Cl. .................................. 205/777.5

(58) Field of Classification Search .................. 205/775, 205/777.5, 792; 204/403.01, 403.14, 403.04, 204/403.09, 403.11, 403.12
See application file for complete search history.

(56) References Cited

U.S. PATENT DOCUMENTS

| | | | |
|---|---|---|---|
| 4,545,382 A | 10/1985 | Higgins et al. | |
| 4,711,245 A | 12/1987 | Higgins et al. | |
| 5,509,410 A | 4/1996 | Hill et al. | |
| 5,628,890 A | 5/1997 | Carter et al. | |
| 5,820,551 A | 10/1998 | Hill et al. | |
| 6,071,391 A | 6/2000 | Gotoh et al. | |
| 6,120,676 A | 9/2000 | Heller et al. | |
| 6,143,164 A | 11/2000 | Heller et al. | |
| 6,299,757 B1 | 10/2001 | Feldman et al. | |
| 6,338,790 B1 | 1/2002 | Feldman et al. | |
| 6,377,894 B1 | 4/2002 | Deweese et al. | |
| 6,461,496 B1 | 10/2002 | Feldman et al. | |
| 6,475,372 B1 * | 11/2002 | Ohara et al. ............. | 205/777.5 |
| 6,503,381 B1 | 1/2003 | Gotoh et al. | |
| 6,514,460 B1 | 2/2003 | Fendrock | |
| 6,540,891 B1 | 4/2003 | Stewart et al. | |
| 6,591,125 B1 | 7/2003 | Buse et al. | |
| 6,592,745 B1 | 7/2003 | Feldman et al. | |
| 6,600,997 B2 | 7/2003 | Deweese et al. | |
| 6,616,819 B1 | 9/2003 | Liamos et al. | |
| 6,618,934 B1 | 9/2003 | Feldman et al. | |

(Continued)

FOREIGN PATENT DOCUMENTS

WO 01/57510 8/2001

OTHER PUBLICATIONS

Pries, et al. (1992) "Blood Viscosity in Tube Flow: Dependence on Diameter and Hematocrit" Am. J. Physiol. 263(6 Pt 2):H1770-H1778.

*Primary Examiner* — Jeffrey T Barton
*Assistant Examiner* — Steven Rosenwald
(74) *Attorney, Agent, or Firm* — Edward J. Baba; Benjamin C. Pelletier; Bozicevic, Field & Francis LLP

(57) ABSTRACT

The present invention provides methods and apparatuses for analyte detection.

19 Claims, 6 Drawing Sheets

U.S. PATENT DOCUMENTS

| | | |
|---|---|---|
| 6,676,816 B2 | 1/2004 | Mao et al. |
| 6,730,200 B1 | 5/2004 | Stewart et al. |
| 6,736,957 B1 | 5/2004 | Forrow et al. |
| 6,749,740 B2 | 6/2004 | Funderburk et al. |
| 6,764,581 B1 | 7/2004 | Forrow et al. |
| 6,773,671 B1 | 8/2004 | Lewis et al. |
| 6,893,545 B2 | 5/2005 | Gotoh et al. |
| 6,942,518 B2 | 9/2005 | Liamos et al. |
| 7,288,174 B2 * | 10/2007 | Cui et al. ................. 204/403.14 |
| 2002/0139692 A1 * | 10/2002 | Tokunaga et al. ........... 205/777.5 |
| 2003/0079983 A1 | 5/2003 | Long et al. |
| 2004/0060818 A1 * | 4/2004 | Feldman et al. ......... 204/403.01 |
| 2004/0232009 A1 * | 11/2004 | Okuda et al. .................. 205/789 |
| 2004/0259180 A1 | 12/2004 | Burke et al. |
| 2005/0287035 A1 | 12/2005 | Yon-Hin et al. |
| 2006/0156796 A1 | 7/2006 | Burke et al. |
| 2006/0231421 A1 | 10/2006 | Diamond et al. |
| 2006/0231423 A1 | 10/2006 | Harding et al. |
| 2007/0062262 A1 | 3/2007 | Blaschke et al. |
| 2007/0235347 A1 * | 10/2007 | Chatelier et al. .............. 205/792 |

* cited by examiner

Abbott Discl. 2006-85

Abbott Discl. 2006-85

Abbott Discl. 2006-85

ANALYTE DETERMINATION METHODS AND DEVICES

CROSS-REFERENCE TO RELATED APPLICATIONS

This application claims the benefit of U.S. Provisional Application No. 60/941,152, filed May 31, 2007, which application is incorporated herein by reference.

BACKGROUND OF THE INVENTION

The detection of the level of analytes, such as glucose, lactate, oxygen, and the like, in certain individuals is vitally important to their health. For example, the monitoring of glucose is particularly important to individuals with diabetes. Measurement of glucose levels is an essential part of diabetes treatment and monitoring, and glucose levels must be constantly monitored so that a diabetic can properly maintain a normal glucose levels and avoid the ill effects of diabetes. To this end, a variety of blood glucose monitoring devices has been developed to help people with diabetes maintain healthy levels of blood glucose. In some devices, a test strip is used to obtain a sample of blood for measurement of the glucose concentration in the sample. The test strip is then inserted into the blood glucose monitoring device, where the concentration of glucose in the blood is measured. The level is then interpreted as either within, above, or below a recommended level, so that the diabetic can take corrective action, if necessary.

Obtaining an accurate blood glucose reading is essential to those with diabetes. If the measurement is inaccurate, the user might take incorrect action to maintain proper blood glucose level, leading to a host of immediate and long-term health problems.

Unfortunately, many factors affect the blood glucose measurement and can cause inconsistent readings. One of these factors is hematocrit, the volume percentage of erythrocytes (red blood cells) in whole blood. See Dorland's Illustrated Medical Dictionary (1974).

Hematocrit levels affect the measurement of blood glucose in several ways. One way is through the effect of hematocrit on blood viscosity. Blood viscosity strongly correlates to hematocrit levels, as the greater the percentage of blood cells in the total blood volume, the more viscous the blood. The viscosity of blood then directly impacts glucose measurements, as these measurements are directly affected by the rate at which analytes and reagents diffuse within a sample chamber, and this rate of diffusion is inversely related to viscosity.

For example, in amperometric measurement methods (which measures the current being passed through a solution to determine the concentration of an analyte), low hematocrits are typically coupled to elevated glucose readings (and vice versa) for two reasons: (1) reduced viscosity increases the mobility of both glucose and the soluble reagents employed to react with it, and (2) reduced oxygen concentration lessens the percentage of electrons originating from glucose which ultimately are sidetracked to oxygen reduction. Both effects result in increased current, and therefore in elevated blood glucose readings. For high hematocrits, blood glucose readings are depressed, as (1) increased viscosity impedes the mobility of glucose as well as reacting strip reagents, and (2) additional glucose-derived electrons are shunted to oxygen.

More advanced testing techniques use coulometry, where the analyte concentration is determined by measuring the total charge consumed or produced during an electrolysis reaction. In coulometric methods, especially those employing an oxygen-insensitive enzyme, both the above sources of error are reduced. Nevertheless, coulometric methods may retain some hematocrit influence. Furthermore, as strip test times decrease to below 5 seconds, a further source of hematocrit dependence peculiar to coulometric methods may become significant. At very rapid test times, glucose stored inside the erythrocyte may not substantially diffuse out of the cell during the assay, leading to increased hematocrit influence.

Furthermore, hematocrit can vary significantly amongst individuals, which leads to inaccurate measurements of blood glucose in methods that provide a universal algorithm to correct for hematocrit dependence.

It is therefore desirable to know the hematocrit in a blood sample, so that a suitable correction can be applied to the blood glucose reading to increase its accuracy. Some efforts to measure hematocrit and correct blood glucose levels based on these measurements have been made; however, most current methods rely upon interelectrode impedance measurements. Impedance measurements are vulnerable to artifacts arising from incomplete filling and variations in electrode area and chamber thickness. Impedance measurements are also subject to interpersonal variation in blood conductivity due to non-hematocrit related effects such as varying salt concentrations. Additionally, to determine a hematocrit electrochemically, a second electrochemical measurement must be completed after the initial measurement for glucose concentration, which adds time to the testing process.

In addition, current technology typically requires a manual determination of whether the sample is of a control solution or a bodily fluid, such as blood. This can be problematic for several reasons; in particular, a patient's poor eyesight or lack of dexterity can make a manual selection to indicate whether the solution is a sample or control solution quite difficult. An error in this manual entry will result in an erroneous average, which can significantly affect a patient's choice of treatment options. For many patients, such manual intervention presents a substantial physical challenge. A distinct issue unrelated to the physical challenge of making such a manual adjustment, is that individuals who are responsible for showing their average glucose (a current function of most monitors) might willfully adjust their average glucose readings by using the low or normal glucose level control solution, and in this way lower, their average glucose level. Such a situation may be encountered when an individual's own actions would render the actual average glucose levels higher than desired. To further illustrate this example, when a teenager consumes food or beverages that violate a strict diet plan, he or she might be able to falsify the average glucose reading by substituting the blood sample with the low or normal glucose level control solution. Thus, manual determination of a control solution remains a substantial problem in patient care.

Therefore, what are needed are improved methods and devices for accurate measurement of blood glucose concentration and determination of a control solution. Of interest are methods and devices for measuring hematocrit in a sample to correct for hematocrit dependence.

SUMMARY OF THE INVENTION

Embodiments of the present invention provide for the aforementioned problems and fill the aforementioned needs by providing methods and apparatuses for determining a hematocrit-corrected value of an analyte in a sample by determining the fill time of the sample on a test strip. Some embodiments of the present invention also provide methods and apparatuses for hematocrit correction in blood glucose concentration measurements by using fill times of test strips to estimate the hematocrit and provide corrected blood glucose concentrations that are more accurate and less dependent on the hematocrit. Some embodiments of the present invention also provide methods for determining whether a sample is a control solution based on the hematocrit level in the sample by using fill times of test strips to estimate the hematocrit and provide determination that the sample is a control solution. Also provided are systems and kits.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

DETAILED DESCRIPTION OF THE INVENTION

Figure 1:
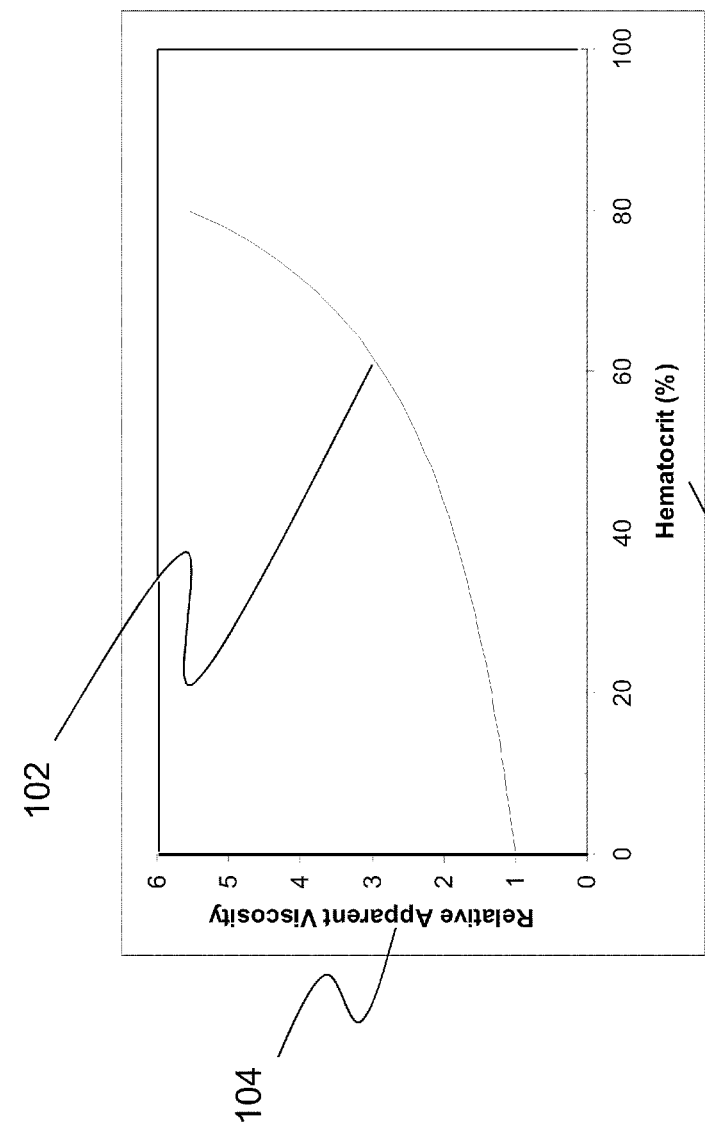
FIG. 1 is a graph depicting a correlation between a hematocrit level and viscosity in blood.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

Embodiments of the present invention provide methods and apparatuses for determining a hematocrit-corrected value of an analyte in a sample by determining the fill time of the sample on a test strip. In one non-limiting embodiment, the method provides for hematocrit correction in a blood glucose concentration measurement by using the fill time of a test strip to estimate the hematocrit and provide a corrected blood glucose concentration that is more accurate and less hematocrit dependent. In another non-limiting embodiment, the method provides for determining whether a sample is a control solution by using fill times of test strips to provide a determination that the sample is a control solution. Since a control solution is equivalent to a blood sample with very low or no hematocrit and therefore the control solution will fill the test strip rapidly. The strong correlation between fill time of a physiological sample in a test strip and hematocrit provides an accurate hematocrit measurement technique, especially when small test volumes are used and quick fill times are needed. The hematocrit correction is particularly beneficial in diabetes self-monitoring, where diabetics are constantly seeking advanced testing equipment that provides more accurate results, requires smaller blood samples and less time to complete the test.

Blood viscosity is a very strong function of hematocrit, as shown in the graph depicted in FIG. 1 (Am. J. Physiol., 1992, 263, H1770-1778). As noted by the plotted line 102, as viscosity of blood 104 increases, so does the percentage of hematocrit 106. The dependence of viscosity on hematocrit continues and becomes even more pronounced at higher hematocrits.

Likewise, the rate at which glucose test strips fill is highly dependent on viscosity. Therefore, strip fill time is also a strong function of hematocrit. Low hematocrit samples fill rapidly, and high hematocrit samples fill slowly. For example, a control solution is equivalent to a blood sample with very low or no hematocrit and therefore the control solution will fill the test strip rapidly. A control solution is generally an aqueous solution that contains a known amount of analyte, such as glucose, and is equivalent to a blood sample with very low or no hematocrit.

Figure 2:
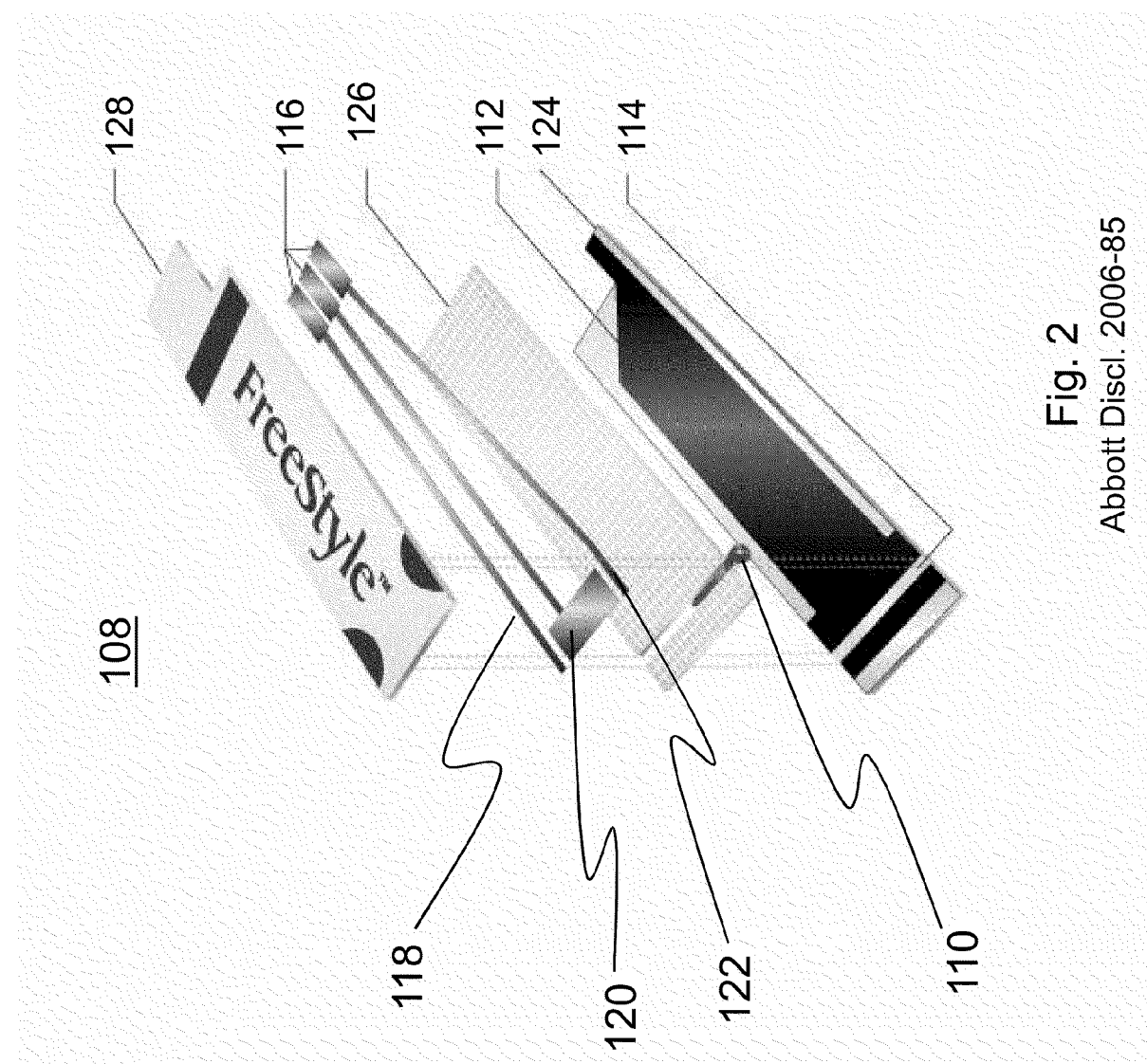
FIG. 2 is an exploded-view illustration of an embodiment of a test strip for the measurement of blood glucose which is capable of determining a hematocrit value based on the fill time of the test strip.

Embodiments of the test strips 108, as illustrated in, for example, the exploded-view embodiment of FIG. 2, measure analyte concentrations using electrochemical techniques. Other techniques are contemplated as well. Embodiments include coulometric and amperometric systems. Embodiments are described herein primarily with respect to coulometric systems, where such descriptions are exemplary only and are in no way intended to limit the scope of the invention. It is also to be understood that embodiments are described primarily with respect to glucose systems in which glucose is the analyte of interest. It is to be understood that embodiments include other analytes. For example, analytes that may be monitored include, but are not limited to, acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times on the same or different test strip.

Any suitable analyte monitoring system may be employed. Systems typically include an analyte test strip and a test strip meter used to read the test strip. For example, analyte monitoring systems that only require small sample sizes, e.g., about 1 microliter or less, e.g., less than about 0.5 microliters, e.g., less than about 0.25 microliters or less, e.g. less than about 0.1 microliters, are contemplated. Short assay time analyte monitoring systems are also contemplated, e.g., systems in which an analyte value may be obtained in about 20 seconds or less, e.g., about 10 seconds or less, e.g., about 5 seconds or less, e.g., about 3 seconds or less. Certain embodiments include Precision® and FreeStyle® blood glucose monitoring systems available from Abbott Diabetes Care, Inc. (Alameda, Calif.). Descriptions of test strips, meters and systems of use in embodiments of the invention may be found in, e.g., U.S. Pat. Nos. 6,071,391; 6,120,676; 6,143,164; 6,299,757; 6,338,790; 6,377,894; 6,600,997; 6,773,671; 6,514,460; 6,461,496; 6,503,381; 6,591,125; 6,592,745; 6,616,819; 6,618,934; 6,676,816; 6,749,740; 6,893,545; 6,942,518; 6,592,745; 5,628,890; 5,820,551; 6,736,957; 4,545,382; 4,711,245; 5,509,410; 6,540,891; 6,730,200; 6,764,581, and elsewhere.

Generally, the test strip meter is equipped with a connector designed to house the test strip and further consisting of contact points configured to contact conductive pads on a distal end of the test strip. When the test strip is inserted into this connector, electrical contact is made and the meter may recognize the act of test strip insertion and turn itself on. Alternatively the user may press a button to turn the meter on.

After the meter is turned on, a blood sample 110 or control solution is introduced into the test strip 108 as illustrated in FIG. 2. The test strip 108 may or may not contain a means for determining that the blood or control solution has completely filled the strip. The meter applies an active potential to a working electrode 112 on the test strip 108, sufficient to initiate the oxidation of glucose (through the agency of a mediator and an enzyme 114). This potential may be applied as soon as the test strip 108 is inserted into the meter, or it may commence only after the test strip 108 is deemed full. After this active potential is applied, electrons originating from glucose in the sample are injected into the working electrode 112, then pass through the meter, where they are counted.

The measurement is in the form of a recorded current versus time. This measurement is continued until such time as the measurement is deemed complete, generally by logical comparison of the recorded current/time curve with a set of conditions stored in the meter software. These conditions might include any of the following (or others): (1) time since current flow began, (2) time since strip deemed full, (3) current as a percentage of peak current, (4) time since peak current, etc. When the set of logical conditions is met, current measurement ceases, and the meter uses its internal logic to calculate a glucose value. This may be accomplished by measuring the current at cessation of measurement, the integrated current (charge) over the lifetime of the measurement, or some hybrid of these two approaches. The meter calculates a single current or charge characteristic of the glucose measurement, and inserts this value into an internal equation to calculate a glucose value. The calculated glucose value is then displayed by the meter.

For certain blood glucose test strips, such as the embodiment illustrated in FIG. 2, the fill time is available from electrochemical current measurements using a working electrode and a counter-reference electrode displaced along the axis of sample flow, wherein one of the electrodes is divided into at least two sub-electrodes whose current can be measured independently. FIG. 2 shows a strip configuration in which the counter-reference electrode 116 (that electrode which passes a current equal in magnitude, but opposite in sign to the working electrode) is divided into three independently measurable sub-electrodes; designated a first sub-electrode 118, second sub-electrode 120, and third sub-electrode 122. In another embodiment (not shown), the working electrode 112 is divided into sub-electrodes instead of the counter-reference electrode. In a further embodiment, the counter-reference electrode 116 or working electrode 112 is divided into only two sub-electrodes. The test strip 108 of the present aspect also includes a bottom layer 124, usually plastic, and adhesive layer 126 in the middle to hold the various components in place, and a top layer 128, usually plastic.

In another embodiment (no shown), a three electrode cell is used, containing a working electrode, a counter electrode, and a reference electrode. In this embodiment, either the working electrode or counter electrode is divided into sub-electrodes for measuring the fill time. The reference electrode could be used to determine fill time, but the mechanism would be different that previously described, as the reference electrode carries no current. In one embodiment the fill time detection on the reference electrode could be potentiometric, wherein the sub-electrodes detect the presence of a potential on the reference electrode.

Figure 3:
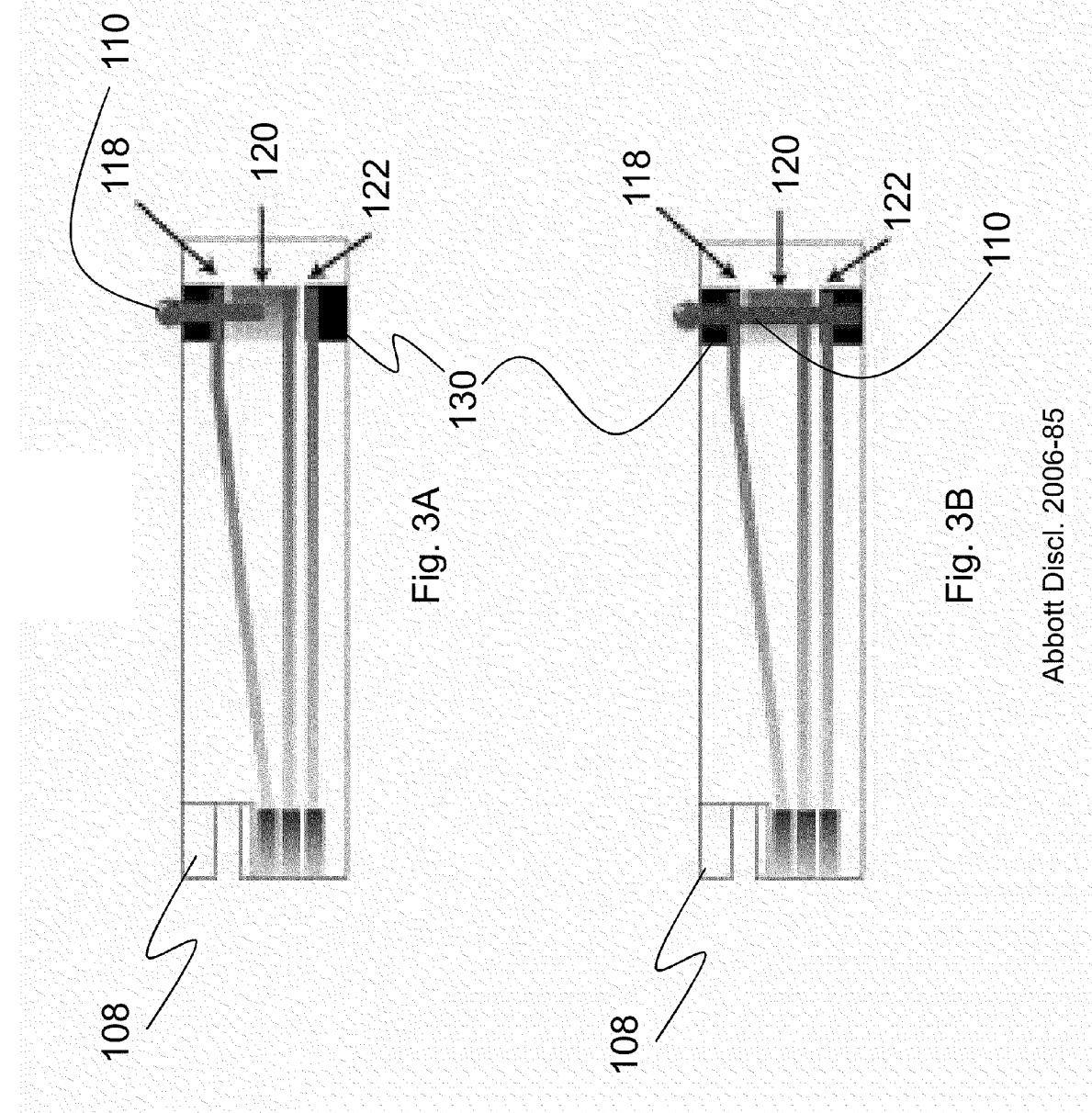
FIG. 3A is an illustration of an embodiment of an electrode configuration in the test strip measuring the fill time of a sample of blood in order to determine a hematocrit value.
FIG. 3B is an illustration of an embodiment of an electrode configuration in the test strip after a sample of blood has completely filled the test strip.

FIG. 3A illustrates the process by which the strip 108 fills with blood 110 or control solution, sequentially contacting the three sub-electrodes. First, blood 110 enters a strip sample area 130, contacting the counter-reference electrode 116. Since the counter-reference electrode is divided into three independent sub-electrodes, the first sub-electrode 118 is contacted first. The blood 110 or control solution continues across the strip sample area 130, next contacting the second sub-electrode 120. Finally, the blood 110 or control solution finishes filling the strip sample area 130, as illustrated in FIG. 3B, contacting the third sub-electrode 122. At each sub-electrode, the time at which the blood sample 110 or control solution contacts the sub-electrode is measurable by the onset of current through that particular sub-electrode. In this way, the time required for blood or control solution to cross the constant and well known inter-electrode distances can be calculated. Other test strip configurations may be used as well. Fewer or greater electrodes than those described herein may be employed. At least two sub-electrodes are needed to measure the hematocrit fill time, from either the working or counter-reference electrodes, although two sub-electrodes of both electrode types, or more than two of either type, are possible as well. While the sub-electrodes in the embodiment described herein are independent for clear measurement of their respective currents, in one embodiment, the main counter-reference electrode is connected at a base and has two extending arms. In this embodiment, slight changes in current are measured at the moment the sample contacts each arm to determine the fill time of the sample. Counter and reference electrode functions may be served by a single counter-reference electrode, and there may be more than one working electrode, reference electrode, and counter electrode. Some or all electrodes of a given test strip may be positioned side-by-side on the same surface of a substrate, or on different surfaces of a substrate, or some or all may be present on another, e.g., second substrate. Additionally, some or all electrodes may be stacked together, may include different materials and dimensions.

Current flows at the displaced electrodes are temporally separated by the fill time. Recently-developed test strips, such as the those for the FreeStyle® blood glucose monitoring device, have three independent counter-reference sub-electrodes, as illustrated in FIGS. 3A and 3B, so two different characteristic fill times can be determined: (1) t1=time from the first sub-electrode 118 to second sub-reference 120, and (2) t2=time from second sub-reference 120 to the third sub-electrode 122, as well as their sum (t3=t2+t1). Fill time data determined from a test strip (e.g., a FreeStyle® test strip) may therefore be used to correct the blood glucose results and thereby reduce the hematocrit dependence.

Figure 4:
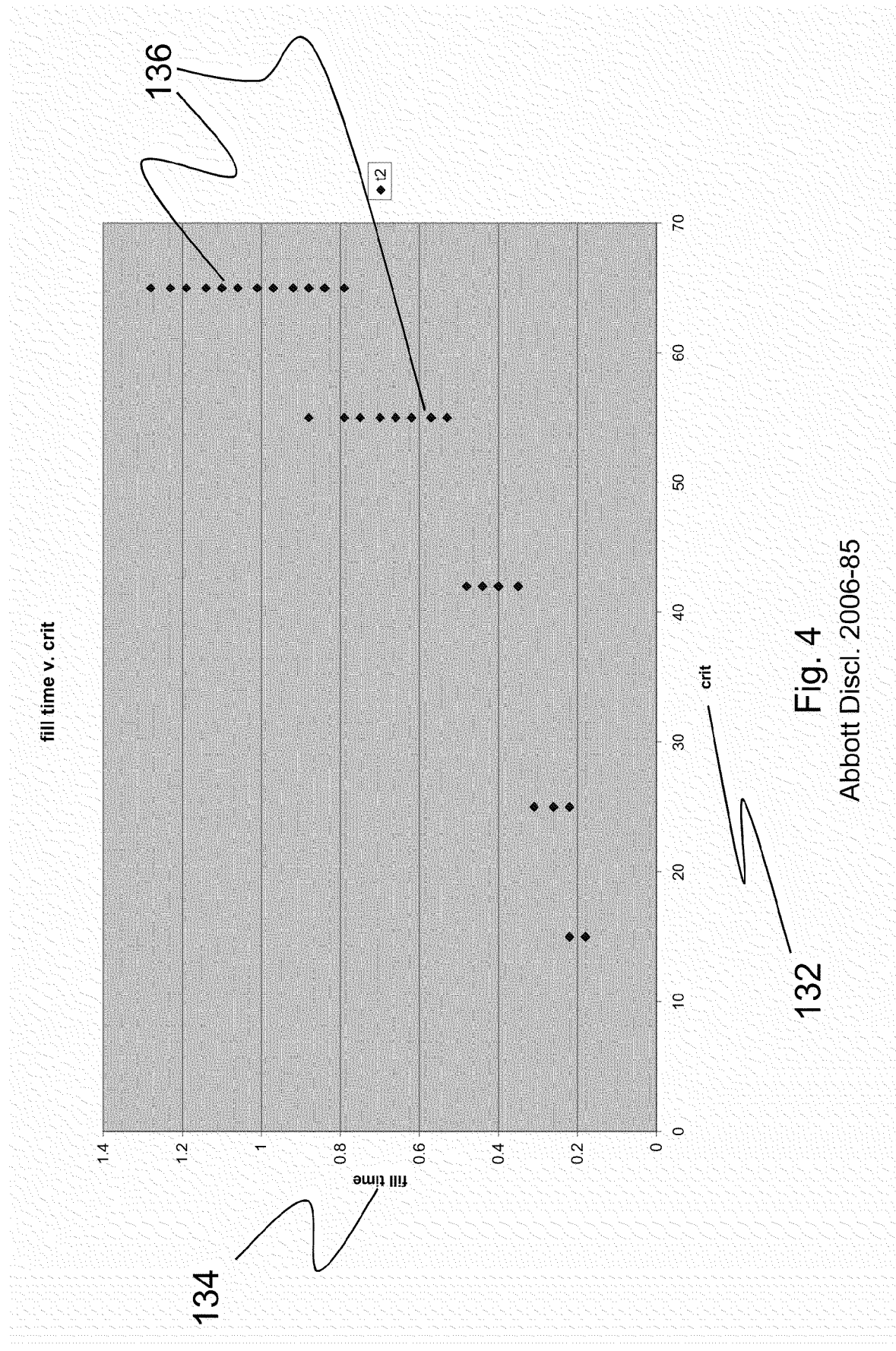
FIG. 4 is a graph depicting a hematocrit dependence of fill time in a test strip embodiment for a physiological sample.
Figure 5:
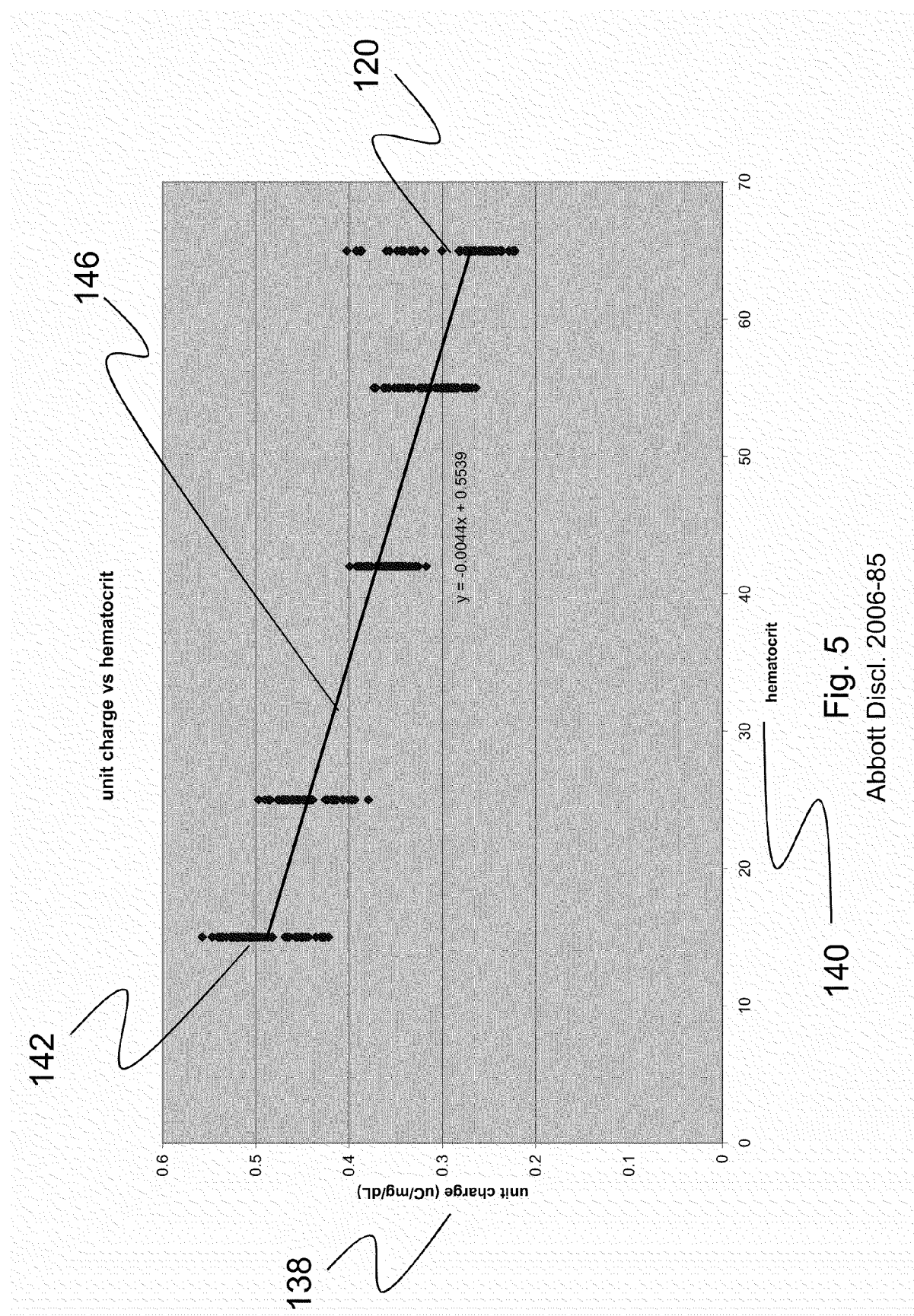
FIG. 5 is a graph depicting a linear regression slope of hematocrit dependence according to embodiments of the present invention.

The dependence of fill time on hematocrit is illustrated in the embodiment of FIG. 4, in which FreeStyle® test strips were tested at a variety of hematocrit values 132, while their fill times 134 were plotted 136 and glucose-related signals were measured (see FIG. 5).

As depicted in FIG. 4, there is a consistent relationship between fill time 134 and hematocrit 132, with fill time 134 increasing as hematocrit 132 increases. Next, the unit charge 138, or response, in uC charge/mg/dL glucose (microCoulombs charge per milligram per deciliter of glucose) for these same strips is plotted in FIG. 5.

Again, the unit charge 138 (proportional to glucose) is elevated at low hematocrit values 140, as depicted by the first measured charge 142, and the unit charge 138 is depressed at high hematocrit values 140, as depicted by the last measured response 144. The measured dependence of the unit response 138 on hematocrit 140, from the slope of the linear regression 146, is about 0.44 percent per hematocrit unit. It is desirable that this slope 146 be decreased, such that the response is not affected by hematocrit.

In accordance with embodiments of the invention, the fill time information is incorporated into the response data in order to correct the response data and lessen its dependence on hematocrit. In one embodiment, the response data is corrected according to the following equation: $R_c=R_r+((Fill\ time-0.4\ s)*R_r)$, where $R_r$ equals the uncorrected response, and Rc equals the corrected response. The value of "(Fill time−0.4 s)" is limited to values less than or equal to 0.2, such that if (Fill time−0.4 s)>0.2, its value is set equal to 0.2. In effect, this limits the positive correction to 20 percent or less.

Figure 6:
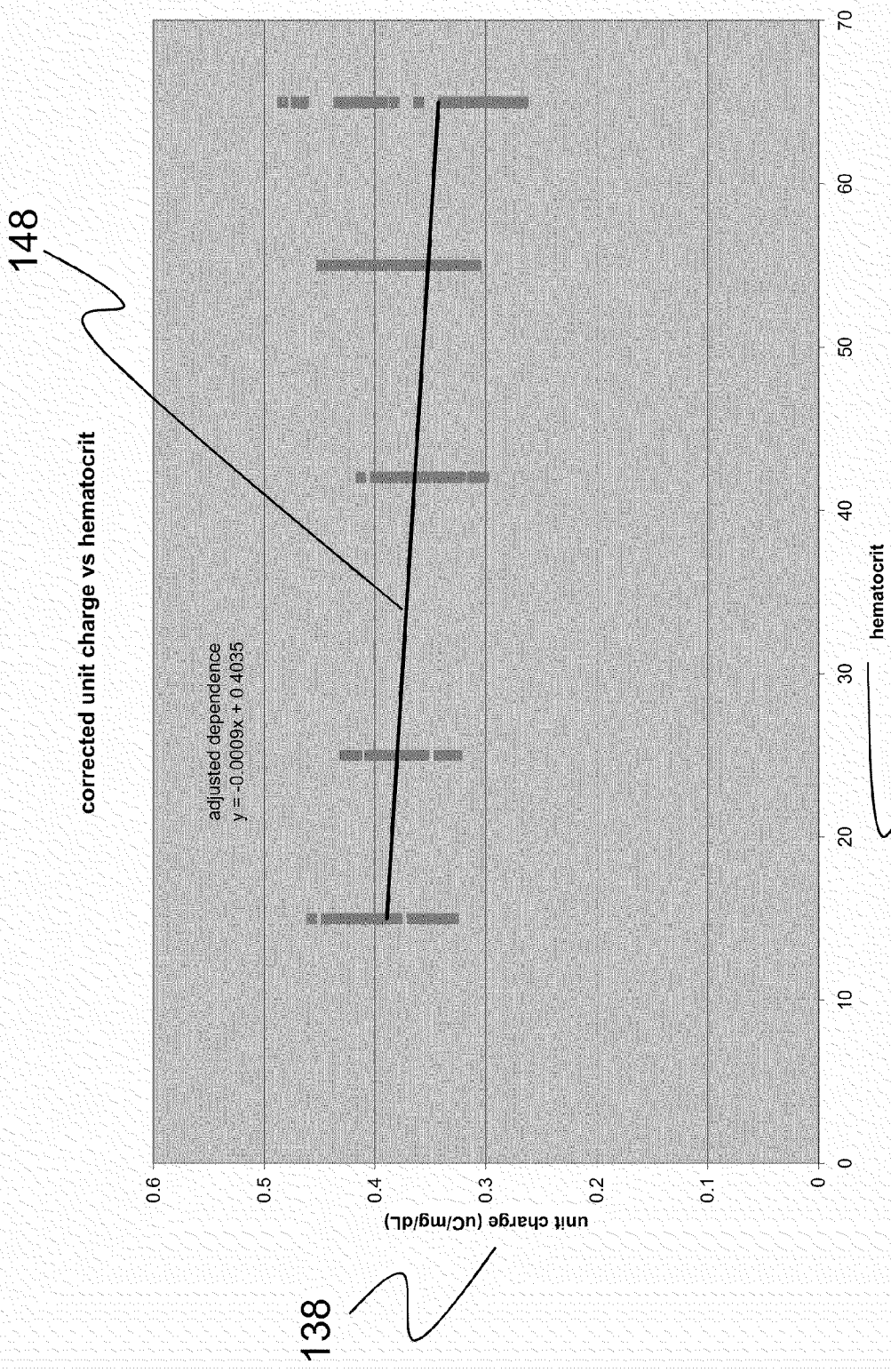
FIG. 6 is a graph depicting a corrected linear regression slope after response data from a glucose measurement was corrected to lessen the hematocrit dependence according to embodiments of the present invention.

The plot of the corrected response factor is shown in FIG. 6. Note that this correction greatly reduces the dependence of the unit charge 138 upon the hematocrit value 140 (the slope of the linear regression 148), from 0.44 percent/hematocrit unit to 0.09 percent/hematocrit unit. Therefore, "hematocrit correction," or application of fill data to correct blood glucose measurements, has successfully reduced the dependence of the glucose measurement upon hematocrit.

In one embodiment, it is determined that a sample is a control solution by using fill times of test strips to provide a determination that the sample is a control solution. Since a control solution is equivalent to a blood sample with very low or no hematocrit and therefore the control solution will fill the test strip rapidly One skilled in the art will appreciate that there are many possible mathematical formulations for determining hematocrit correction, and the equation above is merely an exemplary embodiment. In another embodiment, corrections might be calculated using another of the fill time values available from a test strip, if the test strip provides for multiple fill time measurements.

Additionally, one skilled in the art will appreciate that the test strip does not have to be electrochemical to measure the fill time. In one embodiment, an optical measurement system could be implemented to determine the fill time of the sample on the test strip. Furthermore, in an alternate embodiment, a test module could be used to measure the fill time instead of a test strip. The test module would measure the fill time without the use of a strip, and could be configured to make multiple fill time measurements over time, such as in a laboratory or other clinical setting. The test module could implement an optical or electrochemical measurement system.

In certain embodiments temperature may also affect viscosity (and therefore fill time). Therefore, hematocrit correction based on fill time may also include accurate temperature measurement and compensation. In general, viscosity has in inverse relationship with temperature. As temperature increases, viscosity decreases, and vice versa. Therefore, strips will fill faster at high temperature than at low temperature, if all other factors (chiefly hematocrit) are equal. Fortunately, temperature can be accurately measured and temperature compensation of viscosity is fairly straightforward. The ambient temperature as measured by a temperature sensor in the meter is generally used. The strips are generally at the same temperature as the meter, and the thermal mass of the strips is large compared to the blood sample, so the blood sample is very close to the same temperature as the meter.

In certain embodiments it is also necessary for the blood sample 110 to completely fill the test strip sample area 130 in order to obtain an accurate fill time result, as show in FIG. 3B. A completely filled test strip means the blood sample 110 must contact at least the two of the sub-electrodes, 118 and 122, and the intervening space between them.

Various aspects of embodiments the present invention, whether alone or in combination with other aspects of the invention, may be implemented in C++ code running on a computing platform operating in a LSB 2.0 Linux environment. However, aspects of the invention provided herein may be implemented in other programming languages adapted to operate in other operating system environments. Further, methodologies may be implemented in any type of computing platform, including but not limited to, personal computers, mini-computers, main-frames, workstations, networked or distributed computing environments, computer platforms separate, integral to, or in communication with charged particle tools, and the like. Further, aspects of the present invention may be implemented in machine readable code provided in any memory medium, whether removable or integral to the computing platform, such as a hard disc, optical read and/or write storage mediums, RAM, ROM, and the like. Moreover, machine readable code, or portions thereof, may be transmitted over a wired or wireless network.

Finally, it should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein. The present invention has been described in relation to particular examples, which are intended in all respects to be illustrative rather than restrictive. It is intended that the specification and examples be considered as exemplary only, with a true scope and spirit of the invention being indicated by the following claims.

What is claimed is:

1. A method of determining a hematocrit-corrected value of an analyte in a sample, the method comprising:
    contacting a test strip with a sample comprising an analyte;
    determining an uncorrected value of the analyte $R_r$;
    determining a fill time of the sample on the test strip; and
    calculating a hematocrit-corrected value $R_c$ of the analyte using the equation $R_c=R_r+((\text{fill time}-0.4 \text{ S})*R_r)$.

2. The method of claim 1, wherein said sample is a blood sample.

3. The method of claim 2, wherein said analyte is glucose.

4. The method of claim 1, wherein the fill time of the sample on the test strip is determined using a coulometric method.

5. The method of claim 1, wherein the fill time of the sample on the test strip is determined using an amperometric method.

6. The method of claim 1, wherein the test strip is configured to provide a result using about 1 microliter or less of sample.

7. The method of claim 1, wherein the test strip comprises a working electrode, and a counter-reference electrode, and wherein the working electrode or the counter-reference electrode comprises at least two sub-electrodes whose fill time can be measured independently.

8. The method of claim 7, wherein the fill time of the test strip is calculated by measuring the time for the sample to travel between the first sub-electrode and the second sub-electrode.

9. The method of claim 7, wherein the working electrode or the counter-reference electrode is divided into three independent sub-electrodes: a first sub-electrode, a second sub-electrode, and a third sub-electrode.

10. The method of claim 9, wherein three different fill times are determined on the test strip, wherein a first fill time is determined between the first sub-electrode and the second sub-electrode, a second fill time is determined between the second sub-electrode and the third sub-electrode, and wherein a third fill time is determined between the first sub-electrode and the third sub-electrode.

11. A method for correcting the effect of hematocrit on a blood glucose measurement, the method comprising:
    filling an electrochemical test strip with a blood sample, wherein the test strip is configured to determine a fill time using electrochemical current measurements;
    measuring the fill time of the blood sample on the test strip;
    determining an initial glucose concentration $R_r$ of the blood sample; and
    calculating a corrected glucose concentration $R_c$ of the blood sample using the equation $R_c=R_r+((\text{fill time}-0.4 \text{ S})*R_r)$.

12. A system to determine a hematocrit-corrected value of an analyte, the system comprising:
    a test strip for contacting a sample;
    a meter configured to receive the test strip, wherein the meter is programmed to determine a fill time of the test strip, determine an uncorrected value of the analyte $R_r$, and determine a hematocrit-corrected value of the analyte $R_c$, using the equation $R_c=R_r+((\text{fill time}-0.4 \text{ S})*R_r)$.

13. The system of claim 12, wherein the analyte is glucose.

14. The system of claim 13, wherein the sample is a blood sample.

15. The system of claim 14, wherein the system is configured to provide a hematocrit-corrected value of the analyte using about 1 microliter or less of the sample.

16. The system of claim 12, wherein the meter uses a coulometric method to calculate the hematocrit-corrected value of the analyte.

17. The system of claim 12, wherein the meter uses an amperometric method to calculate the hematocrit-corrected value of the analyte.

18. The system of claim 17, wherein the test strip comprises a working electrode and a counter-reference electrode, and wherein the working electrode or the counter-reference electrode comprises two independent sub-electrodes.

19. The system of claim 18, wherein the two independent sub-electrodes are configured to measure the time required for a sample to move across the test strip from the first sub-electrode to the second sub-electrode, thereby determining a fill time.

* * * * *